United States Patent
Trösken et al.

(10) Patent No.: US 11,110,250 B2
(45) Date of Patent: Sep. 7, 2021

(54) CATHETER WITH CATHETER HUB

(71) Applicant: Phenox Ltd., Galway (IE)

(72) Inventors: Volker Trösken, Witten (DE); Hermann Monstadt, Bochum (DE); Ralf Hannes, Dortmund (DE); David Slattery, Galway (IE); Ken Beatty, Galway (IE)

(73) Assignee: Phenox Ltd., Galway (IE)

( * ) Notice: Subject to any disclaimer, the term of this patent is extended or adjusted under 35 U.S.C. 154(b) by 104 days.

(21) Appl. No.: 16/292,911

(22) Filed: Mar. 5, 2019

(65) Prior Publication Data

US 2019/0275294 A1    Sep. 12, 2019

(30) Foreign Application Priority Data

Mar. 6, 2018  (EP) .................................... 18160214

(51) Int. Cl.
  *A61M 25/00*   (2006.01)
  *A61M 39/10*   (2006.01)
  *A61M 25/10*   (2013.01)

(52) U.S. Cl.
  CPC .... *A61M 25/0097* (2013.01); *A61M 25/0045* (2013.01); *A61M 39/1011* (2013.01); *A61M 25/005* (2013.01); *A61M 2025/0047* (2013.01); *A61M 2025/0062* (2013.01); *A61M 2025/1088* (2013.01); *A61M 2039/1083* (2013.01); *A61M 2039/1088* (2013.01)

(58) Field of Classification Search
  CPC .......... A61M 25/0097; A61M 25/0045; A61M 39/1011; A61M 2025/0047; A61M 25/005; A61M 2025/0062; A61M 2025/1088; A61M 2039/1083; A61M 2039/1088
  See application file for complete search history.

(56) References Cited

U.S. PATENT DOCUMENTS

| | | | | |
|---|---|---|---|---|
| 2001/0034549 | A1* | 10/2001 | Bartholf | A61F 2/95 623/1.12 |
| 2006/0264904 | A1* | 11/2006 | Kerby | A61M 25/0014 604/523 |
| 2017/0151417 | A1* | 6/2017 | Takemura | A61M 39/10 |

* cited by examiner

*Primary Examiner* — Theodore J Stigell
*Assistant Examiner* — Daniel Moore
(74) *Attorney, Agent, or Firm* — Crockett & Crockett, PC; K. David Crockett, Esq.

(57) ABSTRACT

A catheter (1) comprising an elongate tubular body (2) having a proximal end (3), a distal end (4), and an inner lumen (5) extending through the elongate tubular body (2), wherein the elongate tubular body (2) comprises a proximal section (6) and a distal section (7), wherein at least the proximal section (6) comprises at least two layers, wherein the proximal end (3) is connected with a catheter hub (8) being an adapter of greater radial outside dimension than the elongate tubular body (2), wherein the catheter hub (8) has an inner lumen (9) of larger inside diameter than the elongate tubular body (2), and wherein the innermost layer (10) of the proximal section (6) extends into the catheter hub (8) and flares from the proximal section (6) to the catheter hub (8). The catheter ensures a smooth transition of a medical device, e.g. a stent to be transferred from a storage device like a sheath into the tubular body of the catheter.

13 Claims, 2 Drawing Sheets

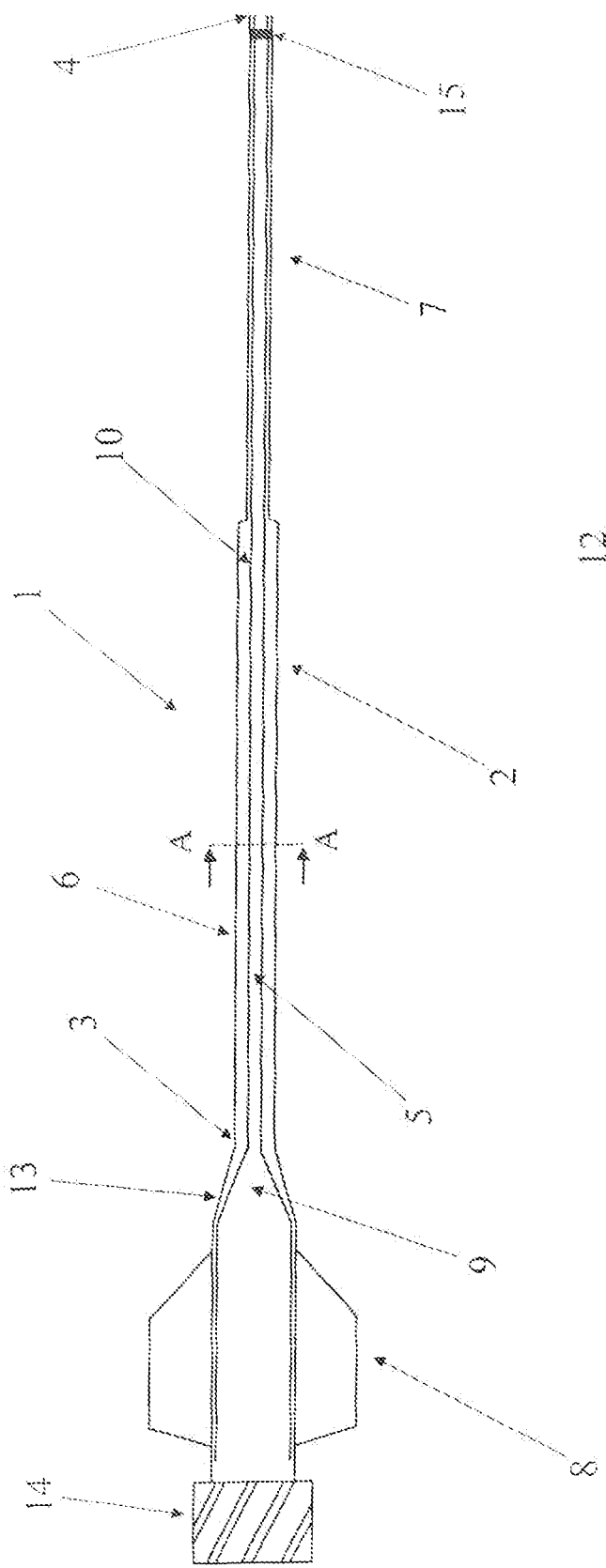
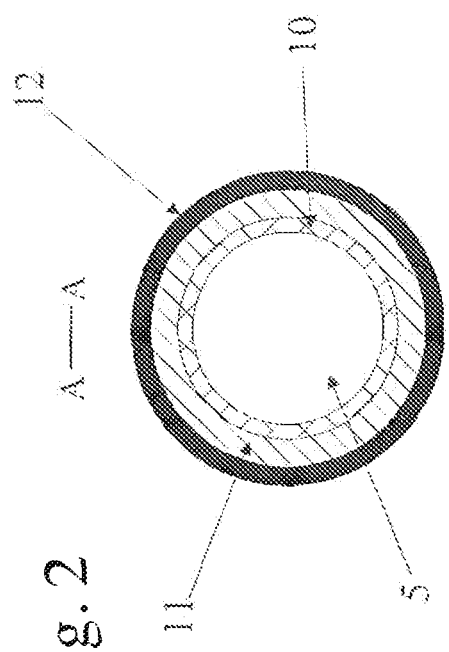

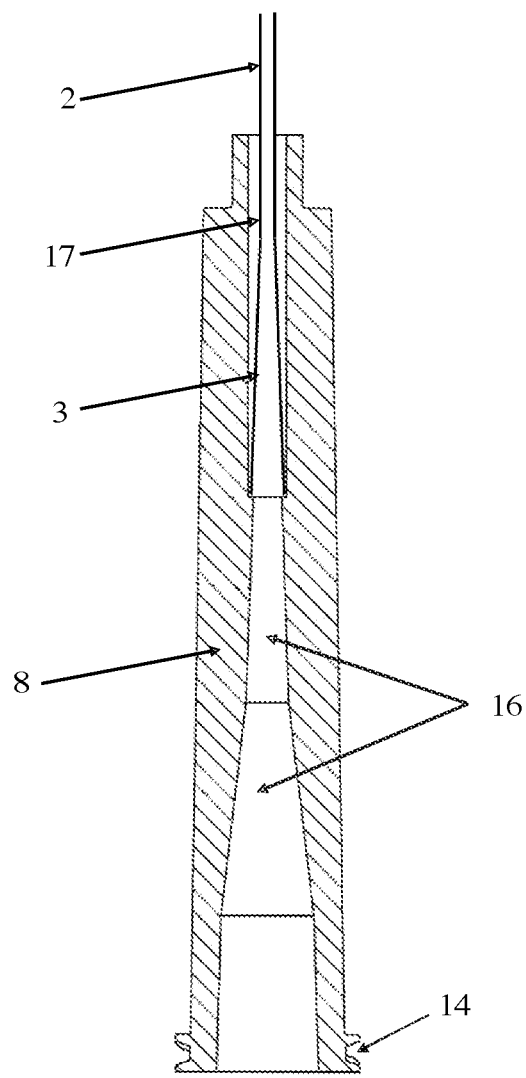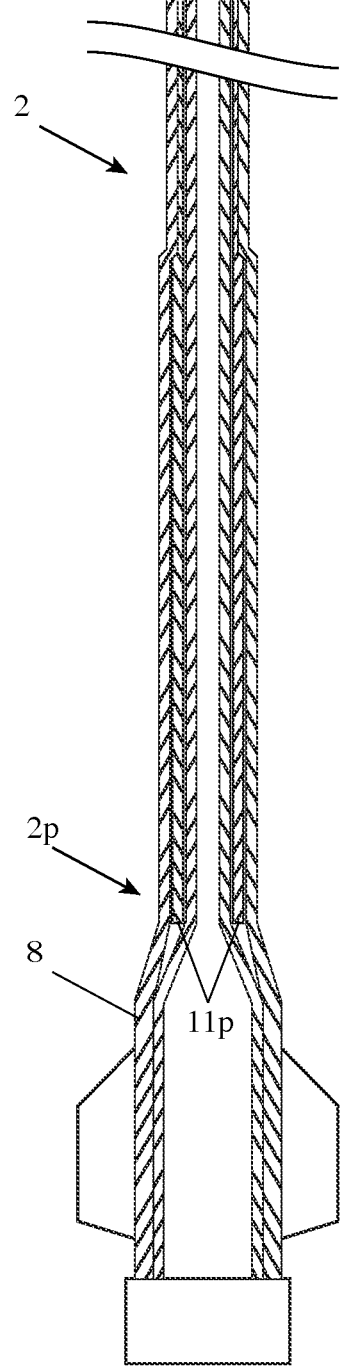

CATHETER WITH CATHETER HUB

The application claims priority to European Patent Application 18160214.5, filed Mar. 6, 2018.

FIELD OF THE INVENTIONS

The application relates to a catheter, in particular to a microcatheter, comprising an elongate tubular body having a proximal end, a distal end, and an inner lumen extending through the elongate tubular body, wherein the elongate tubular body comprises a proximal section and a distal section, wherein at least the proximal section comprises at least two layers, wherein the proximal end is connected with a catheter hub being an adapter of larger radial outside dimension than the elongate tubular body, wherein the catheter hub has an inner lumen of greater inside diameter than the catheter.

BACKGROUND OF THE INVENTIONS

Catheters, in particular microcatheters are tubes to be introduced into the human or animal body. Typically a catheter may be introduced through a blood vessel. Catheters have a proximal end and a distal end, wherein one or more lumens extend from the proximal to the distal end. They may be used to deliver interventional devices such as stents or implants to a target location. They may also be used to deliver diagnostic agents such as contrast media or therapeutic agents such as antiplatelet or vasodilating drugs or other materials to a target location inside the body.

A microcatheter, in particular a microcatheter for intra- and extracranial brain-supplying arteries or intra- or extracranial brain-draining veins, may be inserted through an access in the patient's groin area. First, a guiding catheter is placed. Such a guiding catheter can be delivered through arteries and passageways too large for a microcatheter alone since the microcatheter might bend or become entangled in passageways of large inner diameter. The microcatheter together with a guide wire is inserted into the lumen of the guiding catheter, e.g. through a rotating hemostatic valve, to the distal tip of the guiding catheter. Guidewire and microcatheter are advanced alternately until the desired target site has been accessed. Afterwards the guidewire may be withdrawn from the microcatheter and a medical or interventional device may be inserted into the microcatheter and advanced to the target site. During non-use the medical device may be stored within a storage device like a sheath, however, for insertion into the vascular system the medical device must be transferred from the storage device into the microcatheter.

At the proximal end of the (micro)catheter a catheter hub is typically provided, the catheter hub being an adapter of greater radial outside dimension than the elongate tubular body of the catheter itself. The catheter hub also has an inner lumen that is larger than the inner lumen of the tubular body of the catheter wherein the inner lumen of the catheter hub may, at least in a section of the cather hub, taper from its proximal to its distal end. Such a taper is also called Luer taper, wherein the Luer taper is the female part of a fitting and adapted for insertion of the male fitting of a sheath or other devices. The sheath may comprise the medical device, which can be transferred into the catheter. Having entered the (micro)catheter the medical device will be pushed forward with the help of another guide wire to the target site.

Problems may arise when the medical/interventional device is transferred from the storage device through the catheter hub into the catheter. The medical device, e.g. the stent, contacts the interior of the catheter hub that is typically made of a material with higher coefficient of friction than the interior of the tubular body of the catheter. Furthermore, the catheter hub is frequently made by injection molding and the passage from the catheter hub to the tubular body of the catheter may not always be as smooth as desirable. Finally, in case the catheter hub is connected with the proximal end of the catheter by gluing, minor amounts of adhesive may enter the inner lumen of the catheter. All these factors form an obstacle for the medical device during transfer from the storage device into the catheter. This problem in particular arises in case of self-expandable stents, stent like devices or flow diverters having a tendency to widen and abutting the lumen of the catheter hub and the tubular body. Sometimes it turns out to be necessary to use additional force to push the medical device forward, however, involving the risk of damage or deformation of the medical device.

Accordingly, a need arises for a catheter wherein the transfer of the medical device through the catheter hub into the tubular body is improved.

SUMMARY OF THE INVENTIONS

The problem described above is solved by a catheter comprising an elongate tubular body having a proximal end, a distal end, and an inner lumen extending through the elongate tubular body, wherein the elongate tubular body comprises a proximal section and a distal section, wherein at least the proximal section comprises at least two layers, wherein the proximal end is connected with a catheter hub being an adapter of greater radial outside dimension than the elongate tubular body, wherein the catheter hub has an inner lumen of greater inside diameter than the elongate tubular body, and wherein the innermost layer of the proximal section extends into the catheter hub and flares from the proximal section to the catheter hub.

In the catheter described below, at least the proximal section of the elongate tubular body comprises an innermost layer. However, quite frequently the innermost layer will not only extend through the proximal section but also through the distal section or any optional middle section(s). This innermost layer in the catheter will be extended into the catheter hub wherein the innermost layer flares from the proximal section to the catheter hub. In other words, the inside and outside diameter of the innermost layer within the proximal section of the tubular body is smaller than within the catheter hub and the innermost layer tapers from the catheter hub towards the proximal section of the tubular body. Within the catheter hub the innermost layer may have a cone shape adapted to the taper of the catheter hub. It is not always necessary to apply a taper of the inner lumen of the catheter hub and/or the innermost layer over the complete length of the catheter hub, it will normally also suffice to have a taper in at least one section of the catheter hub.

The catheter described below ensures a smoother transition from the catheter hub to the tubular body reducing the risk of the medical device getting stuck during transfer into the catheter. One reason for this is that any inhomogeneity of the catheter hub or residual adhesive in the transfer region between catheter hub and tubular body will be compensated. Furthermore, the innermost layer of the tubular body normally has a lower coefficient of friction than the catheter hub itself, hence, the medical device will be able to slide more efficiently alongside the innermost layer. The catheter also has advantages in case the medical device shall be removed from the catheter by pulling back. The catheter is of particular value for use in combination with medical devices that are self-expandable since such a self-expandable device has an intrinsic tendency to widen when inserted into the catheter hub.

The innermost layer of the tubular body may extend to the proximal end of the catheter hub, however, this is not absolutely necessary. It does suffice for the innermost layer to extend and flare into the distal end of the catheter hub, so that the medical device may be inserted into the innermost layer.

Typically the innermost layer is a low friction polymer layer. Preferably, the coefficient of friction is below 0.1. The innermost layer may be made for example of polytetrafluoroethylene (PTFE) or perfluoroalkoxy alkane (PFA), however, other polymer layers may also be suitable.

The terms "proximal" and "distal" are well-established in this medical field. When a catheter is inserted into the body the end pointing to the physician is called "proximal" while the end pointing away from the physician is called "distal". In other words, the catheter is pushed forward from proximal to distal.

In preferred embodiments the proximal section and the distal section of the elongate tubular body as well as any optional middle sections comprise at least two layers, wherein the innermost layer of the proximal section also extends through the distal and middle sections. The tubular body, in particular the proximal section, may comprise an outer layer, wherein the outer layer is preferably a polymer layer. The outer layer may, in addition to the innermost layer, extend into the catheter hub and flare from the proximal section to the catheter hub, typically simultaneously to the innermost layer.

Between the outer layer and the innermost layer an intermediate layer may be provided. This intermediate layer may comprise a metal helix or metal meshwork. Typical metals usable for the metal helix/meshwork are stainless steel and nickel-titanium alloys, in particular nitinol. It is possible to provide the proximal section of the elongate tubular body with an intermediate layer with a metal helix/meshwork made of stainless steel and the distal section of the elongate tubular body with an intermediate layer with a metal helix/meshwork made of a nickel-titanium alloy. This ensures a certain stiffness within the proximal section and flexibility within the distal section. However, different combinations of metals, in particular stainless steel and nickel-titanium alloys are possible. Combinations of a metal meshwork in a first section and a metal helix in second section of the elongate tubular body are also conceivable. It is also possible to vary the pitch of the metal helix/meshwork.

In case the outer layer and the innermost layer extend into the catheter hub this may be performed without the intermediate layer comprising the metal helix/metal meshwork. Hence, only the outer layer and the innermost layer flare and extend into the catheter hub while the intermediate layer may end at or near to the proximal end of the tubular body. However, it is also possible that the intermediate layer as well flares and extends into the catheter hub.

While on the one hand a catheter must be stiff enough to be pushed forward over rather long distances of 1 m and more, on the other hand the catheter must be flexible enough to follow the course of small blood vessels. This particularly applies for small blood vessels in the neurovascular field. Furthermore, kink resistance is important. Accordingly, it may be desirable to have a catheter wherein the flexibility of the catheter in the distal section is higher than in the proximal section. Generally, a catheter wherein flexibility increases from the proximal end to the distal end is advantageous. One way to guarantee such flexibility gradient is use of different metals for the metal helix/metal meshwork, another way is to use different materials, in particular polymers, for the proximal, middle and distal section and/or to reduce the outside diameter of the tubular body from proximal to distal. Typical polymer materials usable for manufacturing the catheter are: polyether block amides (PEBA), polyamide copolymers known as Grilamid® and aliphatic polyether-based thermoplastic polyurethanes (TPUs), also known as Tecoflex®.

Moreover, the outside diameter of the tubular body may decrease from proximal to distal, making the distal section of the tubular body more flexible than the proximal section. The outside and the inside diameter of the tubular body may both decrease from proximal to distal wherein decrease may be continuous or stepwise, however, it may also be advantageous just to reduce the outside diameter from proximal to distal and to keep the inside diameter constant in order to avoid any steps or transitions within the tubular body.

As already outlined in the introductory part of the description the catheter hub may comprise an inside Luer taper, tapering from the proximal end to the distal end of the catheter hub. The Luer taper forms the female part of a fitting and is adapted for insertion of the male fitting of other devices.

Preferably the Luer fitting is a Luer lock fitting. This means the Luer fitting is not only a fitting actuated by adherence but also by threads that are suitable for effecting a Luer lock fitting, e.g. to the sheath containing the medical device to be inserted. Typically, the catheter hub comprises threads suitable for being screwed to fitting threads of the counterpart.

The catheter hub may be manufactured from a polycarbonate, polyamide, polypropylene or polyvinylidene fluoride or other polymers. The material used for the catheter hub is stiffer than the material used for the tubular body. The catheter hub may be connected to the proximal end of the elongate tubular body by immediate die injection. As an alternative, the catheter hub may be manufactured separately by injection molding and afterwards connected with the proximal end of the tubular body, e.g. by gluing. The catheter hub may comprise one or more conically shaped steps wherein the inner lumen widens from distal to proximal. Inclination may vary from step to step.

The catheter hub may also comprise a section that is less stiff than the main part of the catheter hub. This section is distal to the main section of the catheter hub adjacent the proximal end of the tubular body. Such a section is known in the literature as strain relief section and has the purpose to avoid kinking of the catheter when advanced. The strain relief section may also comprise a stiffness gradient with decreasing stiffness from proximal to distal.

The distal section of the tubular body may comprise a hydrophilic coating to provide a smooth outer surface. The hydrophilic coating may also be applied partly or completely to an optional middle section or to the proximal section. According to another preferred embodiment the tubular body comprises one or more radiopaque markers for visualization of the catheter within the vessel system. For example such a marker may be made of platinum or platinum-iridium. A marker may be fixed at or near to the distal end of the tubular body.

A typical length of the tubular body is about 110 to 170 cm, preferably about 150 cm. The length of the catheter hub together with an optional strain relief section preferably is about 5 to 7 cm. The outer diameter of the tubular body may be in the range of 0.8 to 1.1 mm, the inner diameter in the range of 0.6 to 0.8 mm. Typically the distal section of the tubular body is shorter than the proximal section. For example, the length of the distal section may be 30 to 40 cm wherein the length of the proximal section may be 70 to 140 cm. A longer proximal section provides sufficient stiffness for being pushed through the vascular system while the more flexible section ensures that the catheter will follow even loopy blood vessels of small inner diameter.

BRIEF DESCRIPTION OF THE DRAWINGS

FIG. 1 shows a side view of the catheter.
FIG. 2 shows a radial cross-section of the catheter according to line A-A of FIG. 1, while FIG. 2A is a longitudinal cross-section of the catheter.
FIG. 3 shows details of the catheter hub design.

DETAILED DESCRIPTION OF THE INVENTIONS

In FIG. 1 the catheter 1 is shown in lateral view. The catheter 1 has an elongate tubular body 2 wherein the proximal end 3 of the tubular body 2 is connected with a catheter hub 8. A radiopaque marker 15 is placed near to the distal end 4 of tubular body 2. The tubular body 2 comprises a proximal section 6 with larger outer diameter and a distal section 7 with smaller outer diameter, whereas the inside diameter of the tubular body is kept constant. A medical device (not shown) may be advanced through the inner lumen 5 of the tubular body 2 to a target site.

The catheter hub 8 has an inner lumen 9 with larger inside diameter that tapers from proximal to distal and forming a Luer taper 13. Furthermore, the catheter hub 8 also comprises threads 14 for being connected with corresponding threads of another device (not shown). The threads 14 serve for establishing a Luer lock connection.

The tubular body 2 comprises an innermost layer 10 shown more in detail in FIG. 2. This innermost layer 10 extends into the catheter hub 8 and flares from the proximal section 6 of the tubular body 2 to the catheter hub 8. The innermost layer 10 is made of a low-friction material, namely PTFE. Hence, a medical device to be introduced into the vascular system through the catheter 1 will slide along the tapering innermost layer 10 smoothly into the tubular body 2 avoiding any edges where pushing the medical device forward may be hampered.

In FIG. 2 the tubular body 2 along line A-A of FIG. 1 is shown in cross section. In this embodiment the tubular body 2 comprises three layers: the innermost layer 10 made of low-friction PTFE that extends and flares into the catheter hub 8, an intermediate layer 11, and an outer layer 12 made of polymer. The intermediate layer 11 comprises a metal meshwork of stainless steel in the proximal section 6 and a metal helix of nickel-titanium alloy in the distal section 7. FIG. 2A illustrates an embodiment of the tubular body 2 in which only the outer layer 12 and the innermost layer 10 flare and extend into the catheter hub 8 while the intermediate layer 11 proximal end 11p terminates proximally at or near to the proximal end 2p of the tubular body 2, such that the intermediate layer does not extend into the catheter hub.

In FIG. 3 the catheter hub 8 is shown in more detail. The tubular body 2 of the catheter extends into the catheter hub 8 wherein the proximal end 3 of the tubular body 2 flares outward. The proximal end 3 comprises at least the innermost layer of the tubular body 2, however, may also comprise further layers. The tubular body 2 is fixed within the catheter hub 8 by adhesive bonding 17.

At the proximal end the catheter hub 8 comprises threads 14 for a Luer lock connection. Furthermore, the catheter hub 8 comprises one or more conically shaped steps 16 within the inner lumen.

The invention claimed is:

1. A catheter comprising an elongate tubular body (2) having a proximal end (3), a distal end (4), and an inner lumen (5) extending through the elongate tubular body (2), wherein the elongate tubular body (2) comprises a proximal section (6) and a distal section (7), wherein at least the proximal section (6) comprises an innermost layer (10), an outermost layer (12) and an intermediate layer (11) disposed between the innermost layer (10) and an outermost layer (12), wherein the proximal end (3) is connected with a catheter hub (8) being an adapter of greater radial outside dimension than the elongate tubular body (2), wherein the catheter hub (8) has an inner lumen (9) of larger inside diameter than the elongate tubular body (2), characterized in that:
the innermost layer (10) of the proximal section (6) extends into the catheter hub (8) and flares from the proximal section (6) to the catheter hub (8); and
the intermediate layer comprises a metal helix or metal meshwork, and the intermediate layer does not extend into the catheter hub.

2. A catheter according to claim 1, characterized in that the innermost layer (10) is a low friction polymer layer.

3. A catheter according to claim 2, characterized in that the low friction polymer layer is a PTFE (polytetrafluoroethylene) or PFA (perfluoroalkoxy alkane) layer.

4. A catheter according to claim 2, characterized in that the proximal section (6) and the distal section (7) of the elongate tubular body (2) comprise at least two layers, the innermost layer (10) being a low friction polymer layer.

5. A catheter according to claim 1, characterized in that the metal helix or metal meshwork is at least partially made of stainless steel.

6. A catheter according to claim 1, characterized in that the metal helix or metal meshwork is at least partially made of a nickel-titanium alloy.

7. A catheter according to claim 1, characterized in that the outermost layer (12) comprises a polymer.

8. A catheter according to claim 7, characterized in that the innermost layer (10) and the outermost layer (12) of the proximal section (6) extend into the catheter hub (8) and flare between the proximal section (6) and the catheter hub (8).

9. A catheter according to claim 1, characterized in that the catheter hub (8) comprises an inside Luer taper (13), tapering from the proximal end to the distal end of the catheter hub (8).

10. A catheter according to claim 9, characterized in that the catheter hub (8) comprises threads (14) that are suitable for effecting a Luer lock fitting.

11. A catheter according to claim 1, characterized in that the catheter hub (8) is connected to the proximal end of the elongate tubular body by injection molding or gluing.

12. A catheter according to claim 1, characterized in that the elongate tubular body (2) tapers from the proximal end (3) to the distal end (4).

13. A catheter according to claim 1, characterized in that the catheter (1) comprises one or more markers (15) made of radiopaque material.

* * * * *